US005766257A

United States Patent [19]
Goodman et al.

[11] Patent Number: 5,766,257
[45] Date of Patent: Jun. 16, 1998

[54] ARTIFICIAL JOINT HAVING NATURAL LOAD TRANSFER

[75] Inventors: Floyd G. Goodman, Williamston; Patrick E. Pringle; Daniel C. Rich, both of Smiths Creek; Louis A. Serafin, Lakeport; Mark E. Stevenson; Cheryl Lynne Warsinske, both of Port Huron Twp., all of Mich.

[73] Assignee: Implant Manufacturing and Testing Corporation, Port Huron, Mich.; by said Patrick E. Pringle, Mark E. Stevenson, Daniel C. Rich and Cheryl Lynne Warsinske

[21] Appl. No.: 790,069

[22] Filed: Jan. 28, 1997

[51] Int. Cl.$^6$ .................................................. A61F 2/38
[52] U.S. Cl. ............................................................ 623/20
[58] Field of Search .................................. 623/16, 18, 20

[56] References Cited

U.S. PATENT DOCUMENTS

| | | | |
|---|---|---|---|
| 4,224,697 | 9/1980 | Murray et al. | 623/20 |
| 4,262,368 | 4/1981 | Lacey | 623/20 |
| 4,301,553 | 11/1981 | Noiles | 623/20 |
| 4,662,889 | 5/1987 | Zichner et al. | 623/20 |
| 4,888,021 | 12/1989 | Forte et al. | 623/20 |
| 5,011,496 | 4/1991 | Forte et al. | 623/20 |
| 5,116,375 | 5/1992 | Hofmann | 623/20 |
| 5,282,867 | 2/1994 | Mikhail | 623/20 |
| 5,314,481 | 5/1994 | Bianco | 623/20 |
| 5,370,701 | 12/1994 | Finn | 623/20 |
| 5,544,689 | 8/1996 | Epstein et al. | 623/20 |

OTHER PUBLICATIONS

Rand et al., J. Bone & Jt. Surgery, "Kinematic Rotating–Hinge Total Knee Arthroplasty," vol.69–A, No. 4, Apr. 1987, 489–497.

Shaw et al., Orthopedics, "Total Knee Arthroplasty Using the Kinematic Rotating Hinge Prosthesis," vol. 12, No. 5, May 1989, 648–654.

Gray et al., "Gray's Anatomy," 1901, 1995 Edition, Barnes and Noble Books, New York, 193 & 251–253.

J. Arthroplasty, vol. 10, Nov. 1995 (Biomat, Inc., FINN knee system ad. plus "Superior Outcome vs. Warfarin" ad diagram).

ASTM F 75–92, 1992.
ASTM F 136–92, 1992.
ASTM F 562–95, 1995.
ASTM F 648–84, 1984.
ASTM F 799–95, 1995.

*Primary Examiner*—Michael J. Milano
*Assistant Examiner*—Tram Anh T. Nguyen
*Attorney, Agent, or Firm*—Christopher John Rudy

[57] ABSTRACT

An artificial joint, generally, can have natural load transfer capabilities. The joint includes a first component having a first articular surface and a rotation device, and a second component having a second articular surface for mating with the first articular surface and a rotation device receptacle. The first component is matable to the second component through cooperation of the rotation device and the rotation device receptacle. The first component can cooperate with the second component in contact of the first and second articular surfaces and in articulation of the joint when the first component is mated to the second component. The joint can be embodied as a knee prosthesis; therein, the first and second components are femoral and tibial components, respectively, with the first articular surface being termed a condylar surface and the second articular surface being termed a condylar mating surface. The joint, especially the rotation device, may be made of metal. The joint may be implanted in suitable bone stock as a prosthesis.

20 Claims, 9 Drawing Sheets

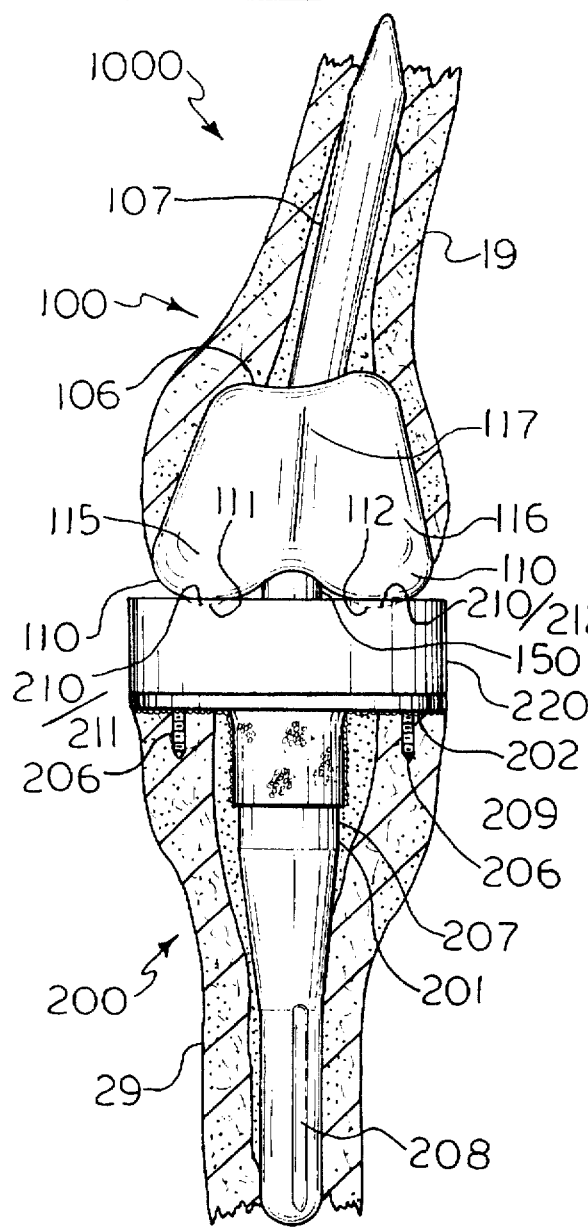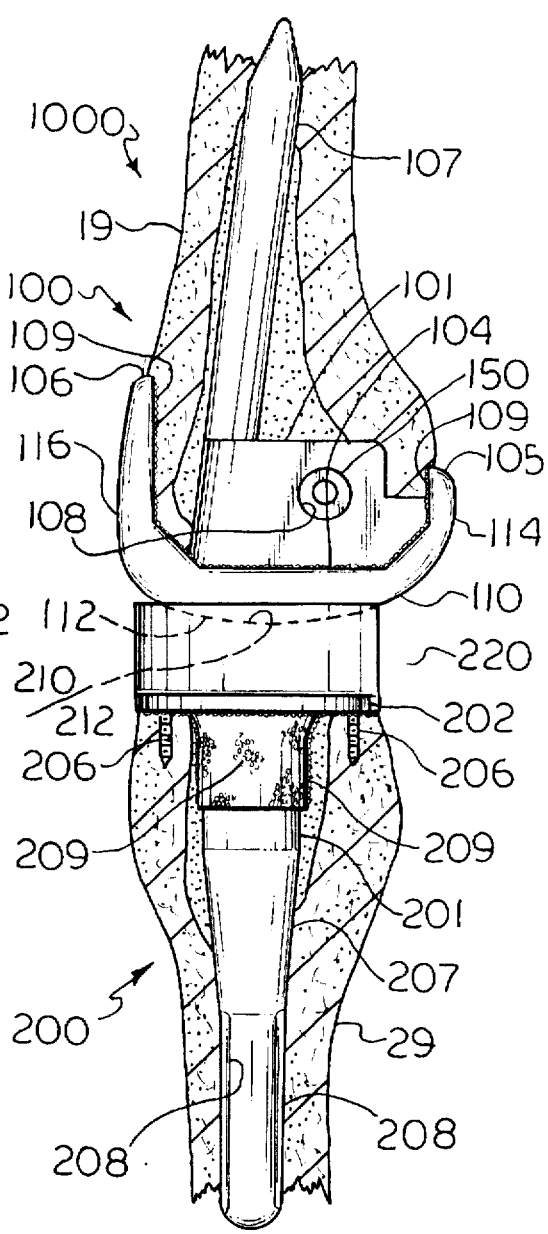

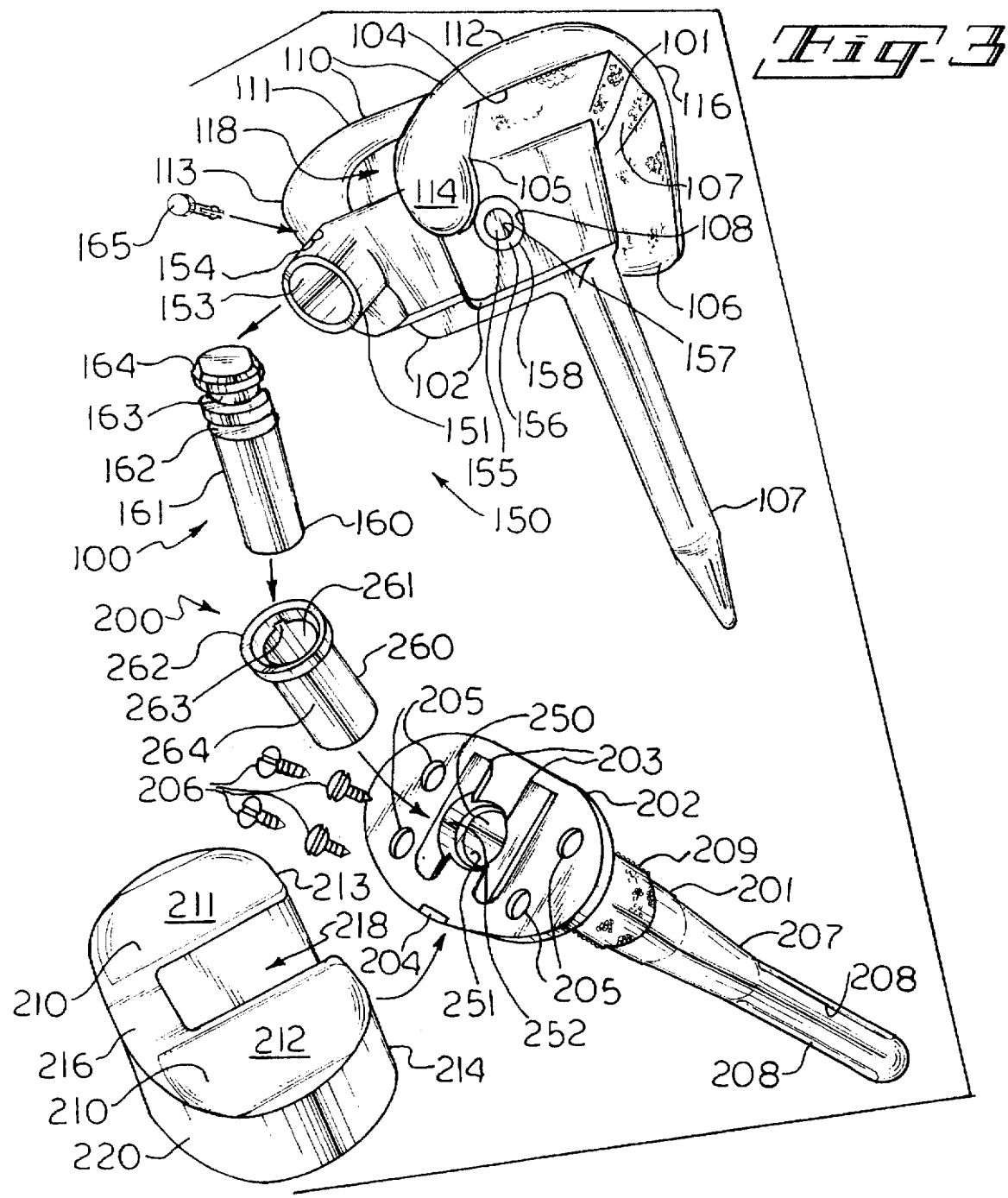

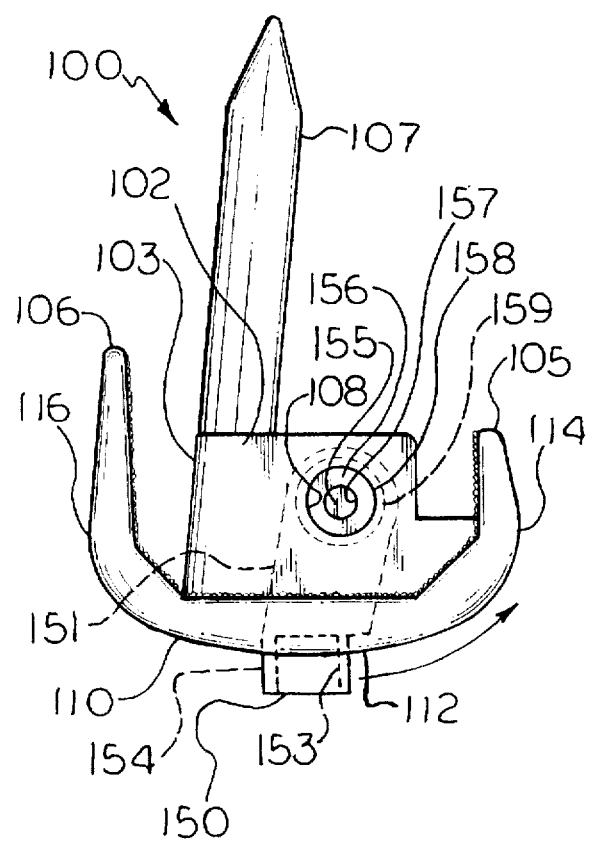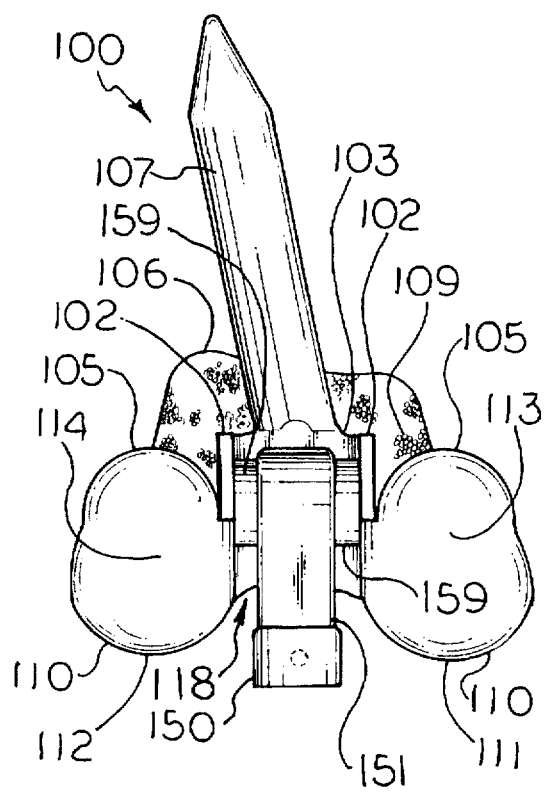

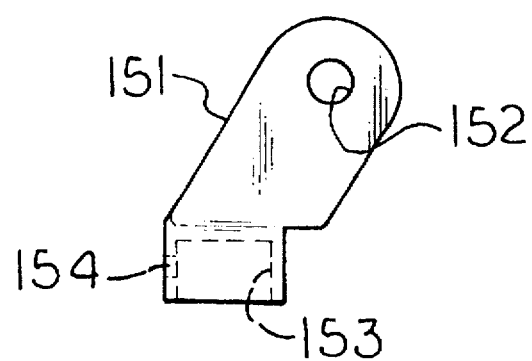
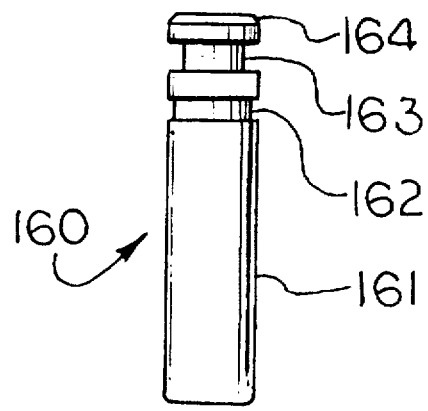

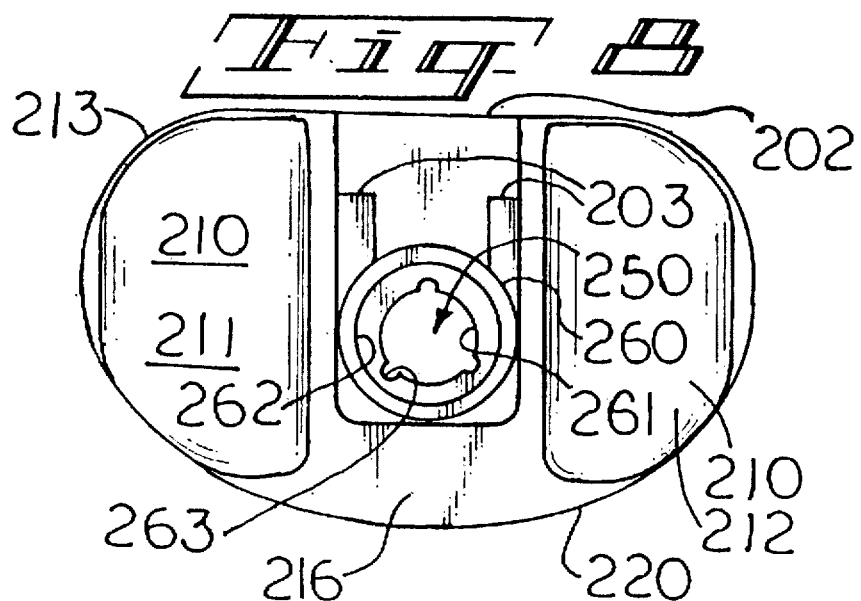
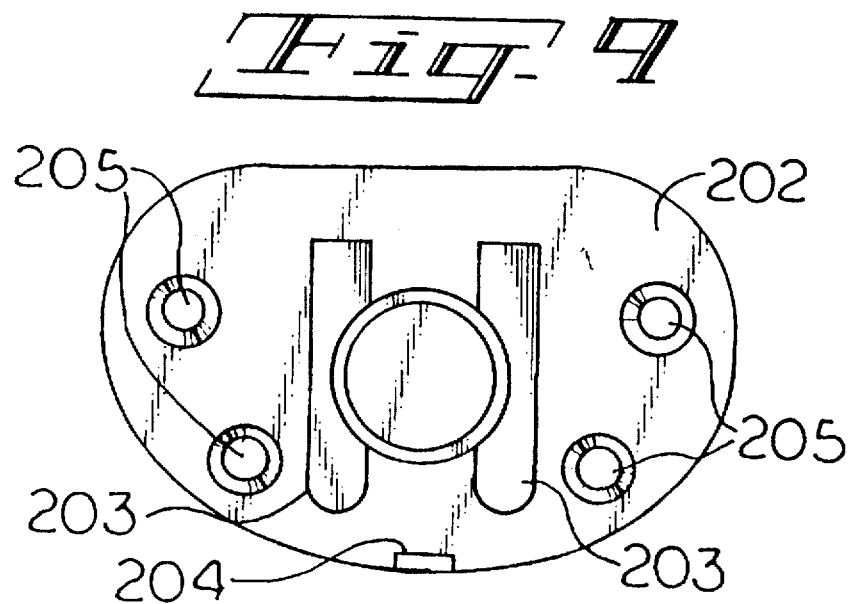

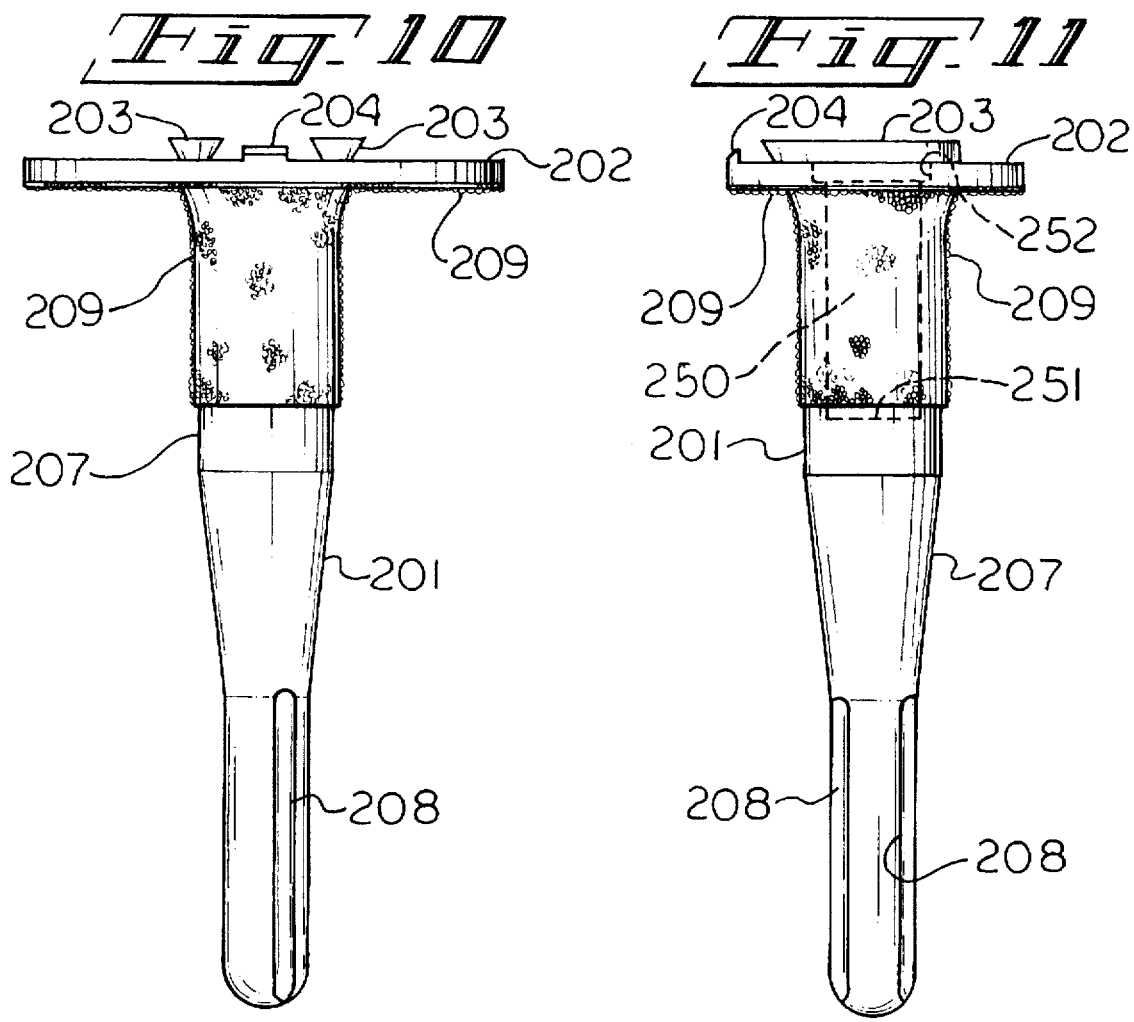

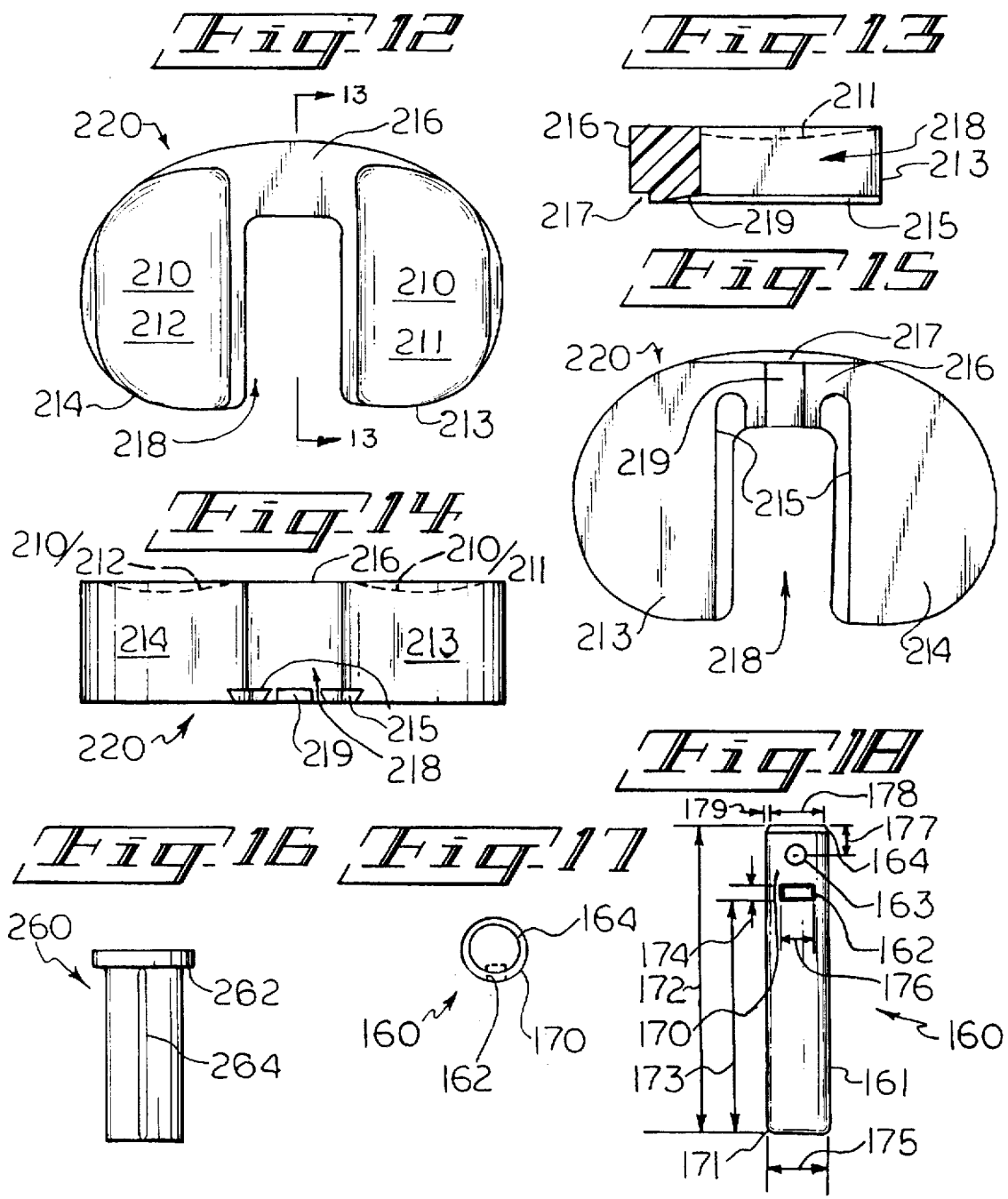

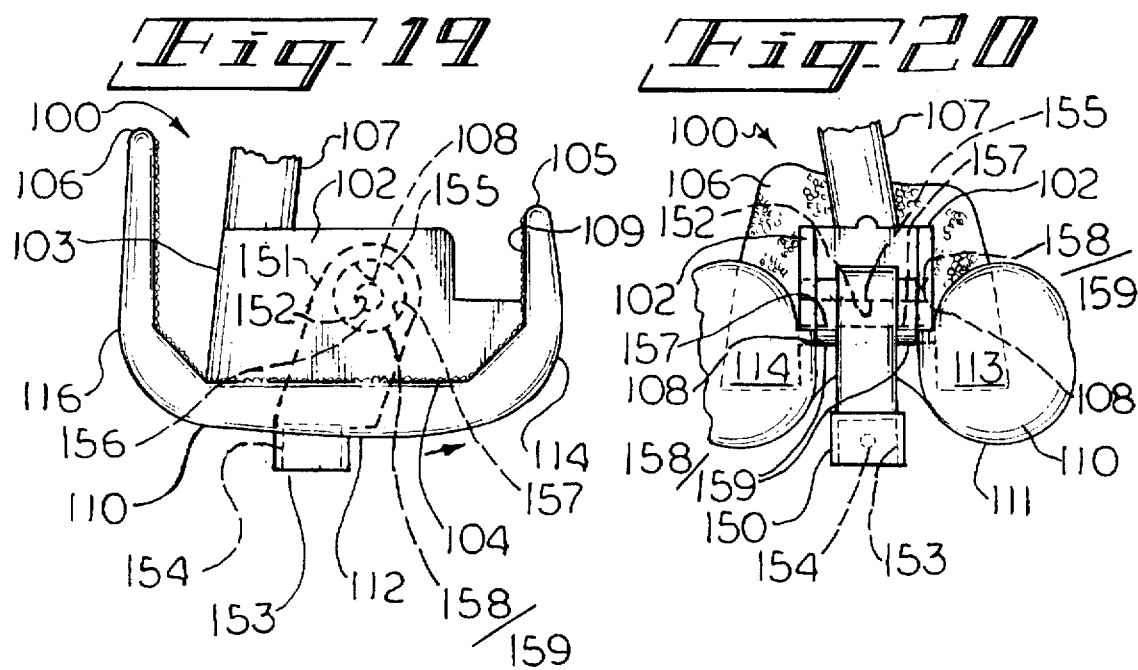

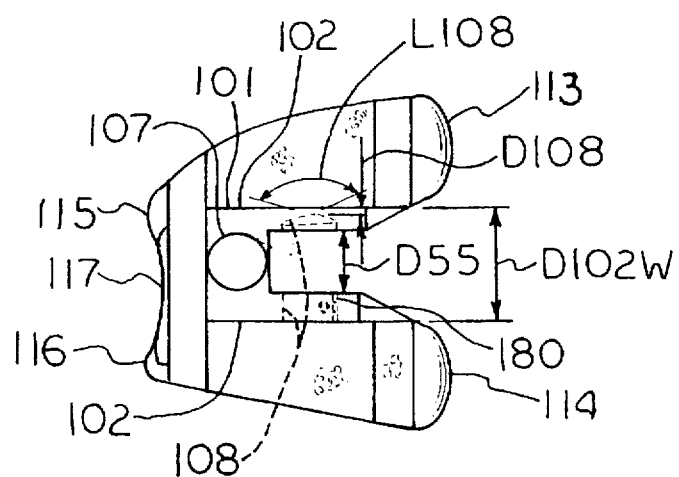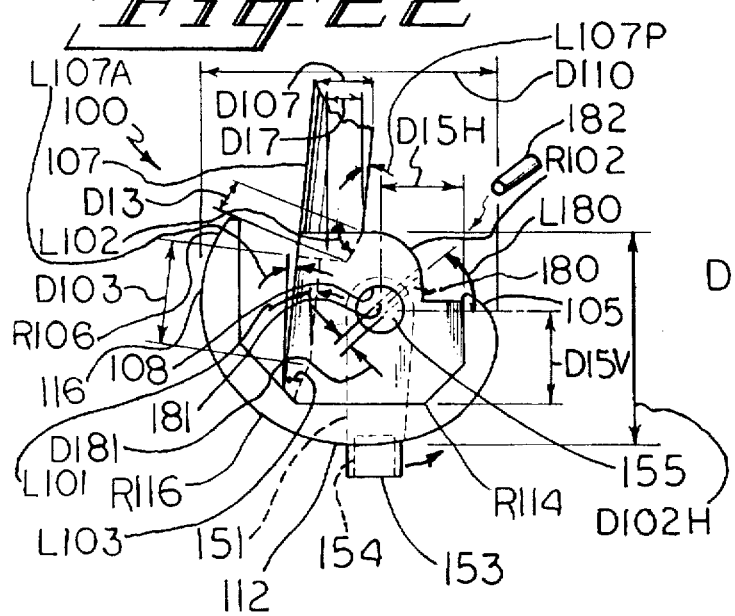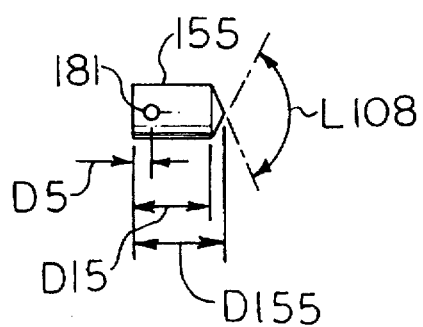

ARTIFICIAL JOINT HAVING NATURAL LOAD TRANSFER

FIELD

The present invention concerns an artificial joint. In one particular embodiment, it concerns a prosthetic knee joint.

BACKGROUND

Various artificial joints and parts thereof are known. For example, one such joint is the FINN (Reg. U.S. Pat. & Tm. Off.) revision/oncology knee system. It may be employed when a patient exhibits significant bone loss, ligamentous deficiencies, primary or metastatic bone tumors, connective tissue disorders, or has undergone several revision arthroplasties. See, *J. Arthroplasty*, Vol. 10, Nov. 1995 (Biomet, Inc., advertisement).

However, problems with such known devices include a certain bulkiness to the prosthesis, which requires significant amounts of bone removal for implantation. Moreover, such devices are known to transfer the load stress through a hinge, which has an altered center of rotation, the presence of which may endanger normal anatomical structures in the posterior compartment of the knee, and which may have a correspondingly limited lifetime and may make for an unnatural gait as well.

It would be desirable to overcome or at least ameliorate such difficulties and problems.

SUMMARY

The present invention provides, in a general embodiment, an artificial joint which generally has natural load transfer capability comprising a first component including a first articular surface and a rotation device; and a second component including a second articular surface for mating with the first articular surface and a rotation device receptacle— said first component matable to said second component through cooperation of the rotation device and the rotation device receptacle, and wherein said first component can cooperate with said second component in contact of the first and second articular surfaces and in articulation of the joint when said first component is mated to said second component. In a more particular embodiment, the joint is a knee prosthesis; therein, said first and second components are femoral and tibial components, with the first articular surface being termed a femoral condylar surface and the second articular surface being termed a tibial condylar mating surface. These surfaces may be considered to be gliding surfaces. Preferably, the joint, especially the rotation device, is of metal construction. Said first and second components may be separate. The joint may be implanted in suitable bone stock.

The invention is useful in arthroplasty, particularly when natural bone and ligament deficiencies exist, and so forth.

Significantly, by the invention, difficulties and problems such as aforesaid are ameliorated if not overcome. In particular application, bulkiness has been reduced from other prostheses, and in an artificial knee the problem of unnatural gait and total knee strategy has been addressed. Thus, the present joint can be implanted with the saving of natural bone. It can transfer load stress in a more natural manner through mating contact of its articular gliding surfaces, rather than primarily through a hinge. The joint more closely restores the kinematics of normal anatomy to reduce the risk of revisional surgery. A more natural articulation to the joint is provided.

Numerous further advantages attend the invention.

DRAWINGS

The drawings form part of the specification hereof. In the drawings, in which like numerals refer to like features, the following is briefly noted:

FIG. 1 is a front view (anterior to posterior direction) of an artificial, prosthetic joint of the invention having natural load transfer, embodied in a total knee replacement implant assembly, shown for a human knee of the left lower limb, implanted in the thigh and leg bones of a human patient.

FIG. 2 is a left side (lateral to medial direction) of the joint of FIG. 1, so implanted.

FIG. 3 is an exploded view of the joint of FIGS. 1 & 2.

FIG. 4 is a left side view (lateral to medial direction) of the femoral component to the joint of FIGS. 1–3.

FIG. 5 is a rear view (posterior to anterior direction) of the femoral component of FIG. 4.

FIG. 6 is a left side view (lateral to medial direction) of the rotation device member of the femoral component in FIGS. 3–5.

FIG. 7 is a side view of the rotation device femoral-tibial taper pin of the joint shown in FIG. 3.

FIG. 8 is a top view (proximal to distal direction) of the tibial component of the joint of FIGS. 1–3.

FIG. 9 is a top view (proximal to distal direction) of part of the tibial component of FIG. 8, with its condylar mating surface tray and rotation device receptacle liner removed.

FIG. 10 is a front view (anterior to posterior direction) of the part of the tibial component of FIG. 9.

FIG. 11 is a left side view (lateral to medial direction) of the part of the tibial component of FIG. 9.

FIG. 12 is a top view (proximal to distal direction) of the condylar mating surface tray of the tibial component of FIG. 8.

FIG. 13 is a part sectional view of the tray of FIG. 12, taken along 13—13 as shown in FIG. 12.

FIG. 14 is a rear view (posterior to anterior direction) of the tray of FIG. 12.

FIG. 15 is a bottom view (distal to proximal direction) of the tray of FIG. 12.

FIG. 16 is a side view of the rotation device receptacle tibial liner of the joint as shown in FIGS. 3 & 8.

FIG. 17 is a top view of another rotation device femoral-tibial taper pin, for employment in the joint shown in FIG. 3.

FIG. 18 is a side view of the rotation device femoral-tibial taper pin of FIG. 17.

FIG. 19 is a left side view (lateral to medial direction) of another embodiment of the femoral component for a joint analogous to that of FIGS. 1–3. This component is essentially all metal.

FIG. 20 is a rear view (posterior to anterior direction) of the femoral component of FIG. 17.

FIG. 21 is a top view (proximal to distal direction) of part of another embodiment of the femoral component for a joint analogous to that of FIGS. 1–3 and 19 & 20.

FIG. 22 is a left, only partially exploded, side view (lateral to medial direction) of a femoral component including the femoral component part shown in FIG. 21. This component is essentially all metal.

FIG. 23 is a side view of a rotation member axle, for employment in the femoral component part and femoral component of FIGS. 21 & 22.

ILLUSTRATIVE DETAIL

The invention can be further understood through the present detail, which may be taken in conjunction with the drawings. The same is to be taken in an illustrative and not necessarily limiting sense.

In reference to the drawings, artificial joint 1000 is shown as a left knee prosthesis for a human being. A corresponding joint for the right human knee could be a mirror image of the left. Other prostheses, for example, elbow, knuckle, hip, and so on, may be provided by analogy to the knee in the practice of the invention. Joints of the invention may be provided with suitable modification for implantation in animals. Since each patient is different, each should be custom fitted. Joints of the invention may be provided for mechanical or robotics applications as well. Accordingly varied can be the joint designs, shapes and sizes, and the materials employed in the practice of the invention.

In general, the joint 1000 includes first component 100 having first articular surface 110 and rotation device 150 and includes second component 200 having second articular surface 210 and rotation device receptacle 250. The first component 100 is matable, i.e., it may be mated, to the second component 200 through cooperation of the rotation device 150 and the rotation device receptacle 250, and, when the first component 100 is mated to the second component 200, the first and second components 100 and 200 are able to cooperate with one another during times when the first articular surface 110 comes in contact with the second articular surface 210 and during articulation (extension, flexion and/or rotation) of the joint 1000. The rotation device 150 can include a swingable, depending male-type part 151, 160 (e.g., FIGS. 3–7, 17–20, 22); the rotation device receptacle 250 can include a female-type part 251, 260 (FIGS. 3, 8, 9, 11, 16), and the first component 100 can be matable to the second component 200 through male-female cooperation of the rotation device 150 and the rotation device receptacle 250. The rotation device 150 can be multi-part, and the rotation device receptacle 250 can be multi-piece. Accordingly, the joint 1000 can have a natural load transfer ability.

As depicted in FIGS. 1–7 & 17–23, the first component 100 may be considered a femoral component for the knee. Generally, it is useful for surgical attachment to femoral bone stock 19.

As a femoral component 100, it can include femoral component frame 101, typically of a one-piece construction of a suitable substance such as of an inert metal, or a suitable engineering plastic or composite. A ceramic substance may be employed. The metal, for example, a cast or forged cobalt-chromium alloy, is preferred. The frame 101 can include side walls 102; front wall 103; distal condylar flange 104; posterior flange 105; anterior flange 106; generally smooth, femoral bone stock insertion stem 107, and wall hole 108 for rotation device 150. Porous, interiorly-facing surface 109 of the metal can face in the proximal and deep directions. The porous surface may be provided by known methods. The first articular surface of the femoral component, i.e., condylar surface 110, of generally convex geometry, generally includes inferior, medial condyle 111; inferior, lateral condyle 112; posterior, medial condyle 113; posterior, lateral condyle 114, and may be considered to include anterior, medial condyle 115, and anterior, lateral condyle 116, although much if not all of the anterior condyles 115 & 116 are restrained from coming into contact with the condylar mating surface 210. On the superficial side of the anterior flange 106 can be provided trochlear surface 117, i.e., the trochlea, on which the actual or an artificial patella, i.e., knee cap, may generally ride. Inter-condylar notch 118 can be formed. Typically, the condylar surface 110 (which includes the condyles 111–116) and the trochlea 117 are smooth and highly polished. The rotation device 150 includes rotation member 151, which has rotation member hole 152; taper pin receptacle 153, which advantageously is formed with a Morse-taper-accommodating cup; and punch-pin hole 154. Axle 155 runs through the hole 152 and, in a developmental embodiment, as illustrated in FIGS. 1–5, through radial bushing 156 of suitable material such as, for example, ultra-high molecular weight polyethylene (UHMWPE) such as would satisfy ASTMF648-84, which bushing has axle hole 157, through which the axle 155 passes; insert shoulder 158, which fits snugly in the wall hole 108; and member-spacing shoulder 159. In this developmental embodiment, employed in the work in hereinafter-presented Examples 1 & 2, the rotation member hole 152 fits tightly around the axle 155 so as to fix the rotation member 151 to the axle 155; ends of the axle 155 are in contact with bushings 156 through holes 157, and the axle 155 rotates therein. The rotation device 150 of the prosthetic knee femoral component 100 is completed by provision of taper pin 160, which includes cylindrical shaft 161; extraction groove 162, used for extracting the pin 160 from the taper pin receptacle 153, for example, with a prying tool, especially during surgical adjustment of the prosthesis 1000; extraction-restriction punch-pin locking groove 163; and taper lock tip 164, which is made with the Morse-taper to fix the pin 160 in the taper pin receptacle cup 153. When the pin 160 is so fixed, it is set by insertion and fit of extraction-restriction and/or rotation-restriction punch-pin 165, which preferably has a head, a shaft, a slit through the shaft extremity so as to provide two compressible-expansible fingers of the shaft, and an extremity knob so as to provide additional holding ability when the punch-pin is set. The punch-pin 165 goes through the punch-pin hole 154 and into the punch-pin locking groove 163. Advantageously, the taper pin 160 and punch-pin 165 are made of the cobalt-chromium alloy with the taper pin 160 highly polished.

As depicted in FIGS. 1–3 & 8–16, the second component 200 may be considered a tibial component for the knee. Generally, it is useful for surgical attachment to tibial bone stock 29.

As a tibial component 200, it can include tibial component frame 201, typically of a one-piece construction of a suitable substance such as of an inert metal, or a suitable engineering plastic or composite. A ceramic substance may be employed. The metal is preferred which may be a cast, or a forged, or, desirably, a drawn or extruded, titanium alloy or the cobalt-chromium alloy. The frame 201 can include tibial tray 202 having a set of dovetail liner-insertion rails 203, liner-stopping ramp lock 204, and screw holes 205 through which can be inserted bone-attaching fasteners 206, for example, screws of the titanium alloy or the cobalt-chromium alloy, during surgical implant as may be deemed necessary or desired; stem 207, which may have a number of, for example, three, distal ribbed grooves 208; and porous metal coating 209, for example, on the underside of the tray 202 and proximal portion of stem 207 to face in the distal and superficial directions, respectively. The second articular surface of the tibial component, i.e., condylar mating surface 210, which are generally of concave geometry in relation to the convex geometry of the condylar surface 110, generally includes superior, medial articular surface 211 and superior, lateral articular surface 212 on medial lobe 213 and lateral lobe 214, respectively. On the underside of each lobe 213 &

214 may be a set of dovetail grooves 215 for sliding along the corresponding dovetail liner-insertion rails 203 on the tibial tray 202; lobe-spanning portion 216 is generally present; notch 217 for locking in cooperation with the liner-stopping ramp lock 204 can be provided, and the lobes 213 & 214 provide for an inter-condylar notch 218 analogous to the inter-condylar notch 118. Ramp 219 may be provided so as to make easier installment over the liner-stopping ramp lock 204. Such features 210–219 may be provided on a separable tibial tray liner 220 of suitable material, for example. UHMWPE. Through the top of the tibial tray 202 and into the tibial component stem 207 is provided the rotation device receptacle 250, which may be, for example. in the form of an essentially cylindrical cup 251 having top shoulder recess 252. Rotation device receptacle liner 260, made of a suitable material which is desirably, in the case where the first, femoral component 100 and the second, tibial component 200 are of materials with differing electromotive force potentials, electrically insulating, for example. UHMWPE, can be inserted into the receptacle 250 and its cup 251 so as to itself receive the taper pin 160. The liner 260 can include taper pin accommodating cup 261; shoulder 262, which can fit the in rotation device receptacle top shoulder recess 252; a number of, for example, three, inside, axially directed grooves 263 to permit exit of entrained body fluids during extension and flexion of the implanted joint 1000 and consequent up and down motion of the rotation device taper pin 160, which fits quite closely although movably within the liner cup 261; and outside, axially directed fluid-escape feature 264, for example, a groove, or possibly hole, to permit escape of liquids and/or gases during insertion of the liner 260 into the receptacle 250, between which there is a close, essentially immovable-during-use fit.

In the knee joint 1000, for example, keeping its articular surfaces 110 & 210 in mind, the position of the rotation device 150 with respect to the rotation device receptacle 250 is of high importance for a smoothly functioning prosthesis. It should not be positioned too far forward nor backward, i.e., anteriorly nor posteriorly, respectively, so that when the first component 100 is mated to the second component 200, extension and flexion of the joint is accomplished with a gliding motion of the condylar surface 110 in contact with the condylar mating surface 210, during which articulative movements the rotation device taper pin 160 may ride up and down. i.e., proximally and distally, respectively, in the rotation device receptacle liner 260. Also, with the pin 160 being generally radially symmetrical, at least in portions where it is insertable into the receptacle 260, the articulative movement of rotation is also able to be provided.

Notably, as depicted in FIGS. 17 & 18, another taper pin 160 has cylindrical shaft 161; extraction slot 162, for example, of a 0.065-inch depth or so; extraction-restriction punch-pin locking hole 163, for example, of a 0.094-inch depth or so, or the feature 163 may be in the shape of the extraction slot 162; taper lock tip bevel 164, for example, of a 0.031-inch by 45-degree shape or so; radially symmetrical top taper portion 170, for example, of a 2.7958-degree half angle; and bottom bevel 171, for example, of a 0.020-inch by 45-degree shape or so. As depicted in FIG. 18, for example, in an 8-mm size, the taper pin 160 may have dimensions as follows: a 1.748-inch or so length 172; a 1.264-inch or so length 173; a 0.100-inch or so length 174; a 0.4985-inch or so diameter 175; a 0.250-inch or so width 176; a 0.193-inch or so height 177; a 0.399-inch or so diameter 178, and a 0.4625-inch or so diameter 179. Of course, these dimensions may vary as needed, especially heights 172 & 173, for example, to 2.366-inch and 1.822-inch or so values, respectively, in a 24-mm size, and, of course, may form a guide to dimensions for the taper pin 160 depicted in FIGS. 3 & 7. The taper pin 160 of FIGS. 17 & 18 has increased strength.

Of significant import, as depicted in FIGS. 19–23, the rotation device 150 is of all-metal construction. The same can be made to be integral with the first component frame 101, which, for example, is part of a femoral component 100 with a majority of its features as illustrated in FIGS. 1–6.

As depicted in FIGS. 19 & 20, the all-metal construction can be provided such as by insertion into rotation device member 151 through rotation member hole 152 and then welding together of the ends of metal axle 155, spacer 156 with axle-accommodating hole 157 and with shoulder 58/159, and the side walls 102 while these axle and spacer parts are inserted in holes 108 in the side walls 102. After-polishing of the welded area, especially on the outsides of the walls 102, is desirably carried out. Glue may be employed in place of welding, especially if the parts are made with an engineering plastic or composite. In this advanced embodiment, the rotation member 151 rotates around the fixed axle 155, and plastic bushings are not present.

As depicted in FIGS. 21–23, the all-metal construction can be provided such as in the device of FIGS. 19 & 20 plus providing thicker side walls 102 for accommodation of a larger diameter hole 108, for example, of a 0.437-inch or so diameter, for rotation device axle 155, for example, of a 0.436-inch or so diameter; an angled end stop for the hole 108; and a restraining pin hole 180, which is aligned to axle hole 181 in the axle 155 so that restraining pin 182 can pass therethrough and restrain the axle 155. The pin 182 can be welded about the side wall 102, which may be ground and polished. The same metal may be employed to lessen any possibility of electrical corrosion which otherwise may occur in metals with unequal electromotive force potentials. Dimensions of the device may vary as needed. The following list, with particular reference to FIGS. 22 & 23, illustrates certain of these, which may be considered to be approximate, in the femoral component 100 and its parts as depicted in FIGS. 21–23, and which may form a guide to or be equivalent dimensions for the femoral component 100 and parts thereof as depicted in FIGS. 1–7, 19 & 20, and, in turn, the tibial component 200 and its parts, as may be appropriate, with dimensions given for a 62-mm-size unit:

| Feature | Dimension Identity |
|---------|---------------------|
| D5 | 0.112-inch distance. |
| D13 | 0.232-inch distance. |
| D15 | 0.576-inch distance. |
| D15H | 0.606-inch hole center locater. |
| D15V | 0.550-inch hole center locater. |
| D17 | 0.275-inch distance. |
| D55 | 0.325-inch distance. |
| D102H | 1.440-inch distance. |
| D102W | 0.775-inch distance. |
| D103 | 0.650-inch distance. |
| D107 | 0.500-inch distance. |
| D108 | 0.100-inch distance. |
| D110 | 2.068-inch distance. |
| D155 | 0.675-inch distance. |
| D181 | 0.101-inch distance. |
| L101 | 5-degree angle. |
| L102 | 71-degree angle. |
| L103 | 75-gegree angle. |
| L-108 | 140-degree angle. |

-continued

| Feature | Dimension Identity |
| --- | --- |
| L107A | 5-degree angle. |
| L107P | 2-degree angle, anterior-posterior; 6-degree angle, medial-lateral. |
| L180 | 45-degree angle. |
| R102 | 0.250-inch radius. |
| R105 | 0.284-inch radius. |
| R106 | 0.257-inch radius. |
| R114 | 0.830-inch radius. |
| R116 | 1.118-inch radius. |

Dimensions can be adjusted to suit the patient. For example, in a larger patient, an 82-mm size femoral component 100 may have 0.786-inch and 0.865-inch D15 & D155 dimensions, and so forth.

Metal to metal construction for contact of the first articular, e.g., condylar, surface 110 and second articular, e.g., condylar mating, surface 210 may also be employed. Although it is recognized that metal to metal contact was initially attempted with artificial joint implants, often the implanted joint could be heard in use. With current materials and close tolerances, however, the metal to metal construction of wearing surfaces may be more practically embodied. Desirably nonetheless, the metals are of the same composition to avoid electrical corrosion or fouling in the patient.

The artificial joint of the invention can be made by known methods. High-technology casting, forging, drawing or extruding, and milling, cutting, drilling, coating, and polishing processes may be employed, particularly to make artificial prosthetic components for surgical implanting. In general, tolerances are close, as those skilled in the art appreciate. With metals, although casting can provide serviceable components, forging or drawing or extruding or wrought annealing and so forth and the like desirably provide(s) the implant components since it has been found that such forged or drawn parts are likely to be stronger and more stress resistant. Thus, smaller metal pins, rotation devices, and so forth, can be provided, which can save more bone in the patient. For example, in the artificial knee joint femoral component 100, a cobalt-chromium alloy may be cast to provide the part, in accordance with ASTM-F-75. However, an alloy may be forged to provide smaller, stronger, and more reliable parts, in accordance with ASTM-F-799 or ASTM-F-562.

The joint of the invention can be attached or implanted by those skilled in the art. The components employed for artificial prostheses in human patients are recommended for cemented use.

The following examples further illustrate the invention.

EXAMPLE 1

A 45-year old human female patient, who had had polio as an infant, during 1951 to 1962 had knee reconstructions (level four extremity involvement). During the 1970s to 1990s, progressive recurvatum of the left knee up to thirty-five degrees developed, with failure at bracing. The patient was crutch dependent, with atrophy and motor weakness of lower extremities, the left greater than the right. In 1993, posterior capsular reconstruction was attempted, which resulted in a 35-degree recurvatum again, instability, degenerative arthritis, and disabling pain.

In July of 1994, a left knee joint prosthesis of the invention (FIGS. 1–16; Lansing Custom Knee semi-constrained total knee device, manufactured by BioPro, Inc., Port Huron, Mich.) was surgically implanted into the femoral and tibial bone stock of the left leg of the patient. The prosthesis had its femoral component made with cast cobalt-chrome alloy to ASTM-F-75, with a metal porous coating on the back side of its condylar surface, which faced, in proximal and deep directions, femoral bone stock; its tibial component made with wrought annealed 6–4 ELI (titanium 6 aluminum 4 vanadium, extra low interstitials) titanium to ASTM-F-136, with a metal porous coating on the bottom of the tibial tray and top of the stem to face, in the distal and surface directions, tibial bone stock; and an UHMWPE femoral component rotation device pin bushing, tibial tray liner, and rotation device receptacle liner. In August of 1995, the patient reported no pain; she was free of assistive devices, and the knee was stable. Her HSS knee scores were noted as follows:

| Pre-operation | 45/100. |
| --- | --- |
| Post-operation | 84/100. |
| Range of motion | 0–120 degrees (excellent functional range). |

A year and a half after the implantation, in the relatively small innovative device for this relatively small patient, the rotation device taper pin, which had been necked down to accommodate the patient, was replaced with a stronger rotation device taper pin of forged cobalt-chrome alloy to ASTM F-592.

EXAMPLE 2

A 73-year old human female patient had, in October of 1992, suffered fracture of the lateral tibial plateau with associated ligament injuries of the right knee. Reconstruction of the knee with internal refixation and bone grafting was carried out, but it ultimately failed. In 1994, the patient demonstrated a 45-degree valgus deformity and 25-degree flexion contracture with both bone and ligament deficiencies, associated with disabling pain. The knee was recalcitrant to splinting or bracing.

In July of 1994, a right knee joint prosthesis of the invention (a mirror image of FIGS. 1–16; Lansing Custom Knee semi-constrained total knee device, manufactured by BioPro, Inc., Port Huron, Mich.) was surgically implanted into right femoral and tibial bone stock of the patient. The right knee prosthesis was made in the same manner employing the same types of materials as was the implanted prosthesis of Example 1. In August of 1995, the patient reported no pain, and she was able to walk acceptably. Her HSS knee scores were noted as follows:

| Pre-operation | 42/100. |
| --- | --- |
| Post-operation | 84/100. |
| Range of motion | 5–135 degrees (nearly full range of motion). |

EXAMPLES 3 ET SEQ.

In July and September of 1996, at least two human patients whose conditions were appropriate for salvage operations had knee joint components of the invention surgically implanted into their femoral and tibial bone stock. The components were inclusive of cobalt-chrome alloy (femoral) and titanium alloy (tibial) but otherwise had metal for UHMWPE bushings in the rotation device, i.e., an all-metal femoral component, and/or the modified taper pin (FIGS. 1–20—or mirror image thereof; Lansing Custom Knee semi-constrained total knee device, manufactured by BioPro, Inc., Port Huron, Mich.). Preliminary results are favorable.

CONCLUSION

The present invention is thus provided. Numerous modifications can be effected within its spirit, the literal claim scope of which is particularly pointed out as follows:

We claim:

1. An artificial joint which generally has natural load transfer capability comprising a first component including a first articular surface and a rotation device, wherein the rotation device includes a swingable, depending male-type part; and a second component including a second articular surface for mating with the first articular surface and a rotation device receptacle, wherein the rotation device receptacle includes a female-type part—said first component matable to said second component through male-female cooperation of the rotation device and the rotation device receptacle, and wherein said first component can cooperate with said second component in contact of the first and second articular surfaces and in articulation of the joint when said first component is mated to said second component, wherein said first and second articular surfaces are such that they can have anatomical gliding contact against one another during anatomical rotation in addition to anatomical flexion and extension.

2. The joint of claim 1, wherein the joint is a knee prosthesis; and said first and second components are femoral and tibial components, respectively, with the first articular surface being a condylar surface and the second articular surface being a condylar mating surface.

3. An artificial joint which generally has natural load transfer capability comprising a first component including a first articular surface and a rotation device; and a second component including a second articular surface for mating with the first articular surface and a rotation device receptacle—said first component matable to said second component through cooperation of the rotation device and the rotation device receptacle, and wherein said first component can cooperate with said second component in contact of the first and second articular surfaces and in articulation of the joint when said first component is mated to said second component, wherein said first and second articular surfaces are such that they can have anatomical gliding contact against one another during anatomical rotation in addition to anatomical flexion and extension, wherein said rotation device includes a member rotatable about an axis of rotation in a portion of said first component and further includes a separable pin which is insertable in the rotation device receptacle of said second component.

4. An artificial joint which generally has natural load transfer capability comprising a first component including a first articular surface and a rotation device; and a second component including a second articular surface for mating with the first articular surface and a rotation device receptacle—said first component matable to said second component through cooperation of the rotation device and the rotation device receptacle, and wherein said first component can cooperate with said second component in contact of the first and second articular surfaces and in articulation of the joint when said first component is mated to said second component, wherein said first and second articular surfaces are such that they can have anatomical gliding contact against one another during anatomical rotation in addition to anatomical flexion and extension, wherein the joint is a knee prosthesis; and said first and second components are femoral and tibial components, respectively, with the first articular surface being a condylar surface and the second articular surface being a condylar mating surface, and wherein said rotation device includes a member rotatable about an axis of rotation in a portion of the femoral component and further includes a generally cylindrical, separable taper-pin, which is insertable and fixable in the rotation device member, and which is insertable in the rotation device receptacle of the tibial component where it can move during anatomical articulation of the joint.

5. An artificial joint which generally has natural load transfer capability comprising a first component including a first articular surface and a rotation device; and a second component including a second articular surface for mating with the first articular surface and a rotation device receptacle—said first component matable to said second component through cooperation of the rotation device and the rotation device receptacle, and wherein said first component can cooperate with said second component in contact of the first and second articular surfaces and in articulation of the joint when said first component is mated to said second component, wherein said first and second articular surfaces are such that they can have anatomical gliding contact against one another during anatomical rotation in addition to anatomical flexion and extension, which is a prosthesis for a human, and which includes as the first component the following:

- a femoral component frame, which includes two side walls connected to a front wall, the same being connectable in proximal and deep directions to distal condylar, posterior and anterior flanges, with said distal flange connected to said posterior and anterior flanges;
- a femoral bone stock insertion stem connected to the femoral component frame in a proximal direction;
- a smooth condylar surface of generally convex geometry connected to the femoral component frame in distal and superficial directions, which includes an inferior, medial condyle; an inferior, lateral condyle; a posterior, medial condyle; a posterior, lateral condyle; an anterior, medial condyle; and an anterior, lateral condyle; plus a trochlear surface on a superficial side of the anterior flange, on which a trochlea may generally ride; said condylar surface being such that an inter-condylar notch is present between medial and lateral condyles; and
- a rotation device connected to the femoral component frame, which includes the following:
  - an angular rotation member having a rotation member hole in a proximal extremity thereto, which hole spans the rotation member in a medial to lateral direction; a taper-pin receptacle with a Morse-taper-accommodating cup in a distal extremity of the rotation member, which cup opens in a distal direction, and the opening of which cup is positioned beyond a bend in the rotation member;
  - an axle passing through the hole which spans the rotation member, which axle is connected to the femoral component frame through holes in the two side walls thereof;
  - a taper-pin inserted into said taper-pin receptacle, which taper-pin includes a cylindrical shaft, a top bevel at a proximal end of the taper-pin, and which includes as the second component the following:

- a tibial component frame, which includes a tibial tray having, on the superior side of the tray, a set of parallel dovetail liner-insertion rails extending in an anterior-posterior direction and a liner-stopping ramp lock, and, through the tibial tray, holes through which can be inserted bone-attaching fasteners; a stem attached generally normal to the tibial tray in a distal direction; and a rotation device receptacle in the form of an essentially cylindrical cup having a top shoulder recess, which receptacle extends into the stem and opens in a superior direction;

a separable condylar mating surface tibial tray liner attached to the tibial component frame superior to the tibial tray, which includes a superior, medial articular surface and a superior, lateral articular surface, on medial and lateral lobes of the member, respectively, and both surfaces of generally concave geometry; a set of dovetail grooves, at least one groove on the underside of each lobe, for sliding along corresponding dovetail liner-insertion rails of the tibial tray; a lobe-spanning portion; and a notch for locking in cooperation with the liner-stopping ramp lock of the tibial tray—wherein the lobes as separated by the lobe-spanning portion provide for an inter-condular notch; and a separable rotation device receptacle liner inserted into the rotation device receptacle, which includes a taper pin accommodating cup and a shoulder, a number of axially directed grooves in the interior of the cup to permit exit of entrained body fluids during implanted use, and a fluid-escape feature to permit escape of fluids during insertion of the rotation device receptacle liner into the rotation device receptacle.

6. The joint of claim 5, which includes in the first component a punch-pin hole passing into a side of said cup of the taper-pin receptacle; at least one groove or slot about the proximal end of the taper pin; and an extraction-restriction punch-pin inserted through the hole which spans the rotation member and into at least one of the at least one groove or slot of the taper-pin.

7. The joint of claim 6, wherein ultra-high molecular weight Polyethylene is employed in a bushing for rotation of the rotation device member of the rotation device fixed to an axle which rotates in the bushing, and ultra-high molecular weight polyethylene is employed in the tibial tray liner, which provides the condylar mating surface, and also, ultra-high molecular weight polyethylene is employed in the tibial cup rotation device receptacle.

8. The joint of claim 7, wherein the femoral component and the tibial component include metals, with the metal of the femoral component being dissimilar to that in the tibial component.

9. The joint of claim 7, wherein the femoral component includes a cobalt-chromium alloy, and the tibial component includes a titanium alloy or a cobalt-chromium alloy.

10. An artificial joint which generally has natural load transfer capability comprising a first component including a first articular surface and a rotation device, wherein the rotation device includes a swingable, depending male-type part; and a second component including a second articular surface for mating with the first articular surface and a rotation device receptacle, wherein the rotation device receptacle includes a female-type part—said first component matable to said second component through male-female cooperation of the rotation device and the rotation device receptacle, and wherein said first component can cooperate with said second component in contact of the first and second articular surfaces and in articulation of the joint when said first component is mated to said second component, wherein said first and second articular surfaces are such that they can have anatomical gliding contact against one another during anatomical rotation in addition to anatomical flexion and extension, and further wherein the rotation device is of all-metal construction.

11. An artificial joint which generally has natural load transfer capability comprising a first component including a first articular surface and a rotation device; and a second component including a second articular surface for mating with the first articular surface and a rotation device receptacle—said first component matable to said second component through cooperation of the rotation device and the rotation device receptacle, and wherein said first component can cooperate with said second component in contact of the first and second articular surfaces and in articulation of the joint when said first component is mated to said second component, wherein said first and second articular surfaces are such that they can have anatomical gliding contact against one another during anatomical rotation in addition to anatomical flexion and extension, and further wherein the rotation device is of all-metal construction, wherein the joint is a human knee prosthesis; said first and second components are femoral and tibial components, respectively, with the first articular surface being a condylar surface and the second articular surface being a condylar mating surface; and said rotation device includes a member rotatable about an axis of rotation in a portion of the femoral component and further includes a generally cylindrical, separable taper-pin, which is insertable and fixable in the rotation device member, and which is insertable in the rotation device receptacle of the tibial component where it can move during articulation of the joint.

12. The joint of claim 11, wherein ultra-high molecular weight polyethylene is employed in a tibial tray liner, which provides the condylar mating surface, and ultra high molecular weight polyethylene is employed in a tibial cup rotation device receptacle.

13. The joint of claim 12, wherein the femoral component includes a cobalt-chromium alloy, and the tibial component includes a titanium alloy or a cobalt-chromium alloy.

14. An artificial joint which generally has natural load transfer capability comprising a first component including a first articular surface and a rotation device; and a second component including a second articular surface for mating with the first articular surface and a rotation device receptacle—said first component matable to said second component through cooperation of the rotation device and the rotation device receptacle, and wherein said first component can cooperate with said second component in contact of the first and second articular surfaces and in articulation of the joint when said first component is mated to said second component, wherein said first and second articular surfaces are such that they can have anatomical gliding contact against one another during anatomical rotation in addition to anatomical flexion and extension, and further wherein the rotation device is of all-metal construction, which is essentially of an all metal construction, and wherein said second component has the second articular surface as an integral part of a one-piece tibial component frame, which includes a tibial tray; a stem attached generally normal to the tibial tray in a distal direction; a rotation device receptacle in the form of an essentially cylindrical cup having a top shoulder recess, which receptacle extends into the stem and opens in a superior direction; and the second articular surface.

15. An artificial joint which generally has natural load transfer capability comprising a first component including a first articular surface and a rotation device; and a second component including a second articular surface for mating with the first articular surface and a rotation device receptacle—said first component matable to said second component through cooperation of the rotation device and the rotation device receptacle, and wherein said first component can cooperate with said second component in contact of the first and second articular surfaces and in articulation of the joint when said first component is mated to said second component, wherein said first and second articular surfaces are such that they can have anatomical gliding contact against one another during anatomical rotation in addition to anatomical flexion and extension, and further wherein the rotation device is of all-metal construction, wherein said rotation device member is rotatable about an axis of rotation which is an axle in the femoral component which is fixed by a restraining pin.

16. An artificial femoral component for a knee comprising the following:

- a femoral component frame, which includes two side walls connected to a front wall, the same being connectable in proximal and deep directions to distal condylar, posterior and anterior flanges, with said distal flange connected to said posterior and anterior flanges;
- a femoral bone stock insertion stem connected to the femoral component frame in a proximal direction;
- a smooth condylar surface of generally convex geometry connected to the femoral component frame in distal and superficial directions, which includes an inferior, medial condyle; an inferior, lateral condyle; a posterior, medial condyle; a posterior, lateral condyle; an anterior, medial condyle; and an anterior, lateral condyle; plus a trochlear surface on a superficial side of the anterior flange, on which a trochlea may generally ride; said condylar surface being such that an inter-condylar notch is present between medial and lateral condyles; and
- a rotation device connected to the femoral component frame, which includes the following:
  - an angular rotation member having a rotation member hole in a proximal extremity thereto, which hole spans the rotation member in a medial to lateral direction; a taper-pin receptacle with a Morse-taper-accommodating cup in a distal extremity of the rotation member, which cup opens in a distal direction, and the opening of which cup is positioned beyond a bend in the rotation member; and a punch-pin hole passing into a side of said cup;
  - an axle passing through the hole which spans the rotation member, which axle is connected to the femoral component frame through holes in the two side walls thereof;
  - a taper-pin inserted into said taper-pin receptacle, which taper-pin includes a cylindrical shaft, a top bevel at a proximal end of the taper-pin, and at least one groove or slot about the proximal end of the taper pin; and
  - an extraction-restriction punch-pin inserted through the hole which spans the rotation member and into at least one of the at least one groove or slot of the taper-pin.

17. The artificial femoral component of claim 16, wherein said rotation device is of all-metal construction.

18. An artificial tibial component for a knee comprising the following:

- a tibial component frame, which includes a tibial tray having, on a superior side of the tray, a set of parallel dovetail liner-insertion rails extending in an anterior-posterior direction and a liner-stopping ramp lock, and, through the tibial tray, holes through which can be inserted bone-attaching fasteners; a stem attached generally normal to the tibial tray in a distal direction; and a rotation device receptacle in the form of an essentially cylindrical cup having a top shoulder recess, which receptacle extends into the stem and opens in a superior direction;
- a separable condylar mating surface tibial tray liner member attached to the tibial component frame superior to the tibial tray, which includes a superior, medial articular surface and a superior, lateral articular surface, on medial and lateral lobes of the member, respectively, and both surfaces of generally concave geometry; a set of dovetail grooves, at least one groove on the underside of each lobe, for sliding along corresponding dovetail liner-insertion rails of the tibial tray; a lobe-spanning portion; and a notch for locking in cooperation with the liner-stopping ramp lock of the tibial tray—wherein the lobes as separated by the lobe-spanning portion provide for an inter-condular notch; and
- a separable rotation device receptacle liner inserted into the rotation device receptacle, which includes a taper pin accommodating cup and a shoulder, a number of axially directed grooves in the interior of the cup to permit exit of entrained body fluids during implanted use, and a fluid-escape feature to permit escape of fluids during insertion of the liner into the rotation device receptacle.

19. An artificial joint which generally has natural load transfer capability comprising a first component including a first articular surface and a swingable, multi-part rotation device; and a second component including a second articular surface for mating with tile first articular surface and a rotation device receptacle—said first component matable to said second component through cooperation of the rotation device and the rotation device receptacle, and wherein said first component can cooperate with said second component in contact of the first and second articular surfaces and in articulation of the joint when said first component is mated to said second component, wherein the joint is such that loading of the joint is essentially through said first and second articular surfaces.

20. The joint of claim 19, wherein said first and second articular surfaces are such that they can have anatomical gliding contact against one another during anatomical rotation in addition to anatomical flexion and extension.

* * * * *

UNITED STATES PATENT AND TRADEMARK OFFICE
CERTIFICATE OF CORRECTION

PATENT NO. : 5,766,257
DATED : June 16, 1998
INVENTOR(S) : Goodman et al.

It is certified that error appears in the above-identified patent and that said Letters Patent is hereby corrected as shown below:

In FIG. 3, upper right hand corner, in the vertically descending series of feature numerals, "101, 116, 107, 108," delete "107" and insert therefor -- 109 --.

In column 14, line 42, delete "tile" and insert therefor -- the --.

Signed and Sealed this

Fifteenth Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.  : 5,766,257
DATED       : June 17, 1998
INVENTOR(S) : Goodman et al.

It is certified that error appears in the above-identified patent and that said Letters Patent is hereby corrected as shown below:

Column 2,
Line 12, after "side" insert -- view --.
Line 17, delete "to" and insert therefor -- of --.
Line 38, delete "part" and insert therefor -- partial --.
Line 56, delete "17." insert therefor -- 19. --.

Column 4,
Line 63, delete "are" and insert therefor -- is --.

Column 5,
Line 22, insert hyphens between "taper" and "pin" and between "pin" and "accommodating."
Line 23, delete "the in" and insert therefor -- in the --.

Column 11,
Lines 20-21, insert hyphens after "taper" and "pin."
Line 30, insert a hyphen between "taper" and "pin."
Line 35, change "Polyethylene" to read -- polyethylene --.

Column 12,
Line 17, before "wherein" insert -- and --.

Column 13,
Line 52, insert a hyphen between "taper" and "pin."

Column 14,
Lines 31-32, insert hyphens after "taper" and "pin."

Signed and Sealed this

Fifth Day of August, 2003

JAMES E. ROGAN
*Director of the United States Patent and Trademark Office*